United States Patent [19]  [11] 3,962,254
Mathison et al.  [45] June 8, 1976

[54] N-SUBSTITUTED-5,6-DIHYDROXYCYCLOPENTANO[h]-1,2,3,4-TETRAHYDROISOQUINOLINES AND ETHERS AND ESTERS THEREOF

[75] Inventors: Ian William Mathison; William Ebenezer Solomons, both of Memphis, Tenn.; Raymond Henry Jones, Northport, N.Y.

[73] Assignee: Marion Laboratories, Inc., Kansas City, Mo.

[22] Filed: Mar. 28, 1974

[21] Appl. No.: 455,671

[52] U.S. Cl. ............... 260/287 CF; 260/240 G; 260/286 R; 260/286 Q; 260/289 C; 260/570.5 CA; 260/591; 260/599; 260/611 F; 260/617 F; 424/258
[51] Int. Cl.² ............... C07D 217/16; C07D 217/18
[58] Field of Search .... 260/287 R, 287 CF, 289 CA

[56] References Cited
UNITED STATES PATENTS

| | | | |
|---|---|---|---|
| 1,942,108 | 1/1934 | Laska et al. | 260/287 R |
| 3,282,943 | 11/1966 | Landgraf et al. | 260/287 CF |
| 3,318,896 | 5/1967 | Pribyl et al. | 260/289 C |
| 3,567,733 | 3/1971 | Nomine et al. | 260/287 R |
| 3,798,225 | 3/1974 | Kreighbaum | 260/283 SY |

FOREIGN PATENTS OR APPLICATIONS 1,912,944  10/1970  Germany ............... 260/287

OTHER PUBLICATIONS
Burger, "Medicinal Chemistry," pp. 42, 497.
House, "Modern Synthetic Reactions," 1965 p. 34.
Morrison et al., "Organic Chemistry," 1966 pp. 473–475.
March, "Advanced Organic Chemistry," 1968 p. 414.

*Primary Examiner*—Raymond V. Rush
*Assistant Examiner*—David E. Wheeler
*Attorney, Agent, or Firm*—Merriam, Marshall, Shapiro & Klose

[57] ABSTRACT

N-substituted cyclopentano[h]-1,2,3,4-tetrahydroisoquinolines of the formula

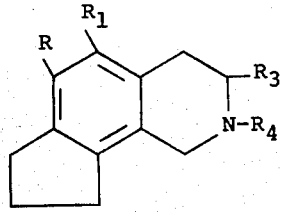

wherein R and $R_1$ represent hydroxy, lower alkoxy, lower akanoyloxy or aryl-lower alkanoyloxy groups, $R_3$ represents hydrogen or a lower alkyl group and $R_4$ represents a lower alkyl, arylcarbonyl, aryl-lower alkyl, benzhydryl-lower alkyl, lower alkanoyl, aryl-lower alkanoyl, benzhydryl-lower akanoyl or benzhydrylcarbonyl group, and acid addition salts and quaternary ammonium salts thereof, and pharmaceutical compositions containing the compounds useful for lowering blood pressure in animals.

24 Claims, No Drawings

N-SUBSTITUTED-5,6-DIHYDROXYCYCLOPENTANO[H]-1,2,3,4-TETRAHYDROISOQUINOLINES AND ETHERS AND ESTERS THEREOF

This invention relates to novel chemical compounds and their production. More particularly, this invention provides novel N-substituted cyclopentano [h]-1,2,3,4-tetrahydroisoquinolines, processes for producing the compounds, novel intermediates useful in making the compounds, and novel pharmaceutical compositions containing the compounds useful for effecting desirable pharmacological activity in animals.

According to one aspect of the subject invention there is provided novel N-substituted cyclopentano [h]-1,2,3,4-tetrahydroisoquinolines of Formula 1

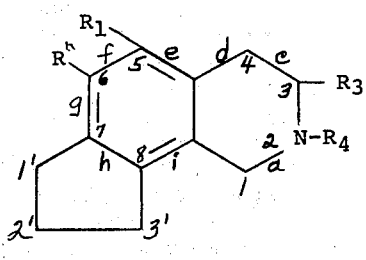

Formula 1 wherein R and $R_1$ are hydroxy, lower alkoxy, lower alkanoyloxy or aryl-lower alkanoyloxy groups, $R_3$ is hydrogen or a lower alkyl group, and $R_4$ is a lower alkyl, arylcarbonyl, aryl-lower alkyl, benzyhydryl-lower alkyl, lower alkanoyl, aryl-lower alkanoyl, benzhydryl-lower alkanoyl or benzhydrylcarbonyl group, and acid addition salts and quaternary ammonium salts of those compounds which form such salts.

The term "lower alkyl" as used herein includes straight or branched chain alkyl groups having 1 to 8, and advisably 1 to 6, carbon atoms such as methyl, ethyl, n-propyl, isopropyl, n-butyl, sec-butyl, n-pentyl, isopentyl and n-hexyl.

The term "aryl" as used herein includes the phenyl group and phenyl groups containing one to three nuclear substituents selected from (1) lower alkoxy groups such as the methoxy and ethoxy groups, (2) lower alkyl groups such as the methyl and ethyl groups, (3) halo groups including the chloro, bromo and fluoro groups, (4) the hydroxy group and (5) the amino group.

The term "benzhydryl" includes the benzhydryl group and benzhydryl groups having, on one or both of the phenyl rings, one to three nuclear substituents selected from (1) lower alkoxy groups such as the methoxy and ethoxy groups, (2) lower alkyl group such as the methyl and ethyl groups, (3) halo groups including the chloro, bromo and fluoro groups, (4) the hydroxy group and (5) the amino group.

The term "lower alkanoyl" includes saturated, monovalent groups derivable from monocarboxylic acids, including straight and branched groups having 1 to 8, and advisably 1 to 6, carbon atoms, such as formyl, acetyl, propionyl, α-methylpropionyl, butyryl and hexanoyl.

The term "lower alkanoyloxy" includes saturated monovalent groups from monocarboxylic acids, including straight and branched groups, having 1 to 8, and advisably 1 to 6, carbon atoms such as formyloxy, acetoxy, propionyloxy and butyryloxy.

The N-substituted-5,6-dialkoxycyclopentano[h]-1,2,3,4-tetrahydroisoquinolines of Formula 2

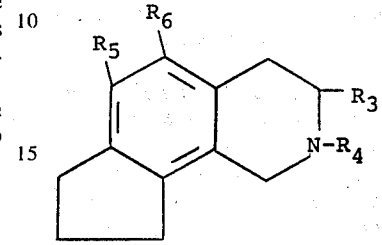

Formula 2 wherein $R_5$ and $R_6$ are lower alkoxy, and $R_3$ and $R_4$ have the assigned significance but $R_4$ has at least 2 carbons, all of which compounds come within Formula 1, can be produced by reacting a 5,6-di-lower alkoxycyclopentano[h]-1,2,3,4-tetrahydroisoquinoline with an alkanoyl halide, an aryl-lower alkanoyl halide or a benzhydryl-lower alkanoyl halide to produce an

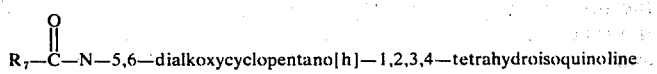

which is then reduced to the $R_4$-N-5,6-dialkoxycyclopentano[h]-1,2,3,4-tetrahydroisoquinoline. This process can be represented as follows:

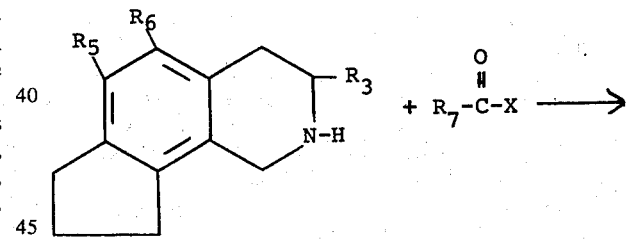

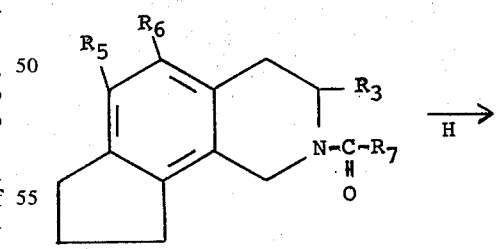

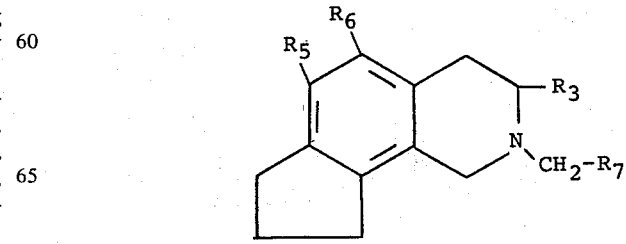

wherein $R_3$, $R_4$, $R_5$ have the previously assigned significance, X is a reactive halo group such as the bromo and chloro groups and —$CH_2$—$R_7$ equals $R_4$.

Some of the tetrahydroisoquinolines which can be used as starting materials in the described process are 5,6-dimehoxycyclopentano[h]-1,2,3,4-tetrahydroisoquinoline, 5,6-diethoxycyclopentano[h]-1,2,3,4-tetrhydroisoquinoline, 5,6-dipropoxycyclopentano[h]-1,2,3,4-tetrahydroisoquinoline and 5-methoxy-6-ethoxycyclopentano[h]-1,2,3,4-tetrahydroisoquinoline.

Some alkanoyl halides and aryl substituted alkanoyl halides which can be used in the first step of the process are acetyl chloride, propionyl chloride, butyryl bromide, benzoyl chloride, p-methoxybenzoyl chloride, 3,4-dimethoxybenzoyl chloride, 3,4,5-trimethoxybenzoyl chloride, diphenylacetyl chloride, diphenylpropionyl bromide, 3,4-dimethoxyphenylacetyl chloride, 4-methylbenzoyl chloride, 4-fluorophenylacetyl chloride and 3,4-diethoxybenzoyl chloride.

Reaction between the tetrahydroisoquinoline and alkanoyl halide, or aryl-substituted alkanoyl halide, to form the desired amide is readily effected by bringing the reactants together in an inert liquid reaction medium, such as benzene or toluene, in the presence of an acid binding agent, such as triethylamine. Heating of the mixture, such as at reflux temperature, increases the reaction rate. After the reaction is terminated the amide reaction product can be isolated from the reaction mixture by conventional procedures.

Representative of the amides which can be produced as described from the appropriate reactants are N-acetyl-5,6-dimethoxycyclopentao[h]-1,2,3,4-tetrahydroisoquinoline, N-propionyl-5,6-diethoxycyclopentano[h]-1,2,3,4-tetrahydroisoquinoline, N-(3,4-dimethoxybenzoyl)-5,6-dimethoxycyclopentano[h]-1,2,3,4-tetrahydroisoquinoline, N-(3,4-dimethoxyphenylacetyl)-5,6-dimethoxycyclopentao[h]-1,2,3,4-tetrahydroisoquinoline, N-(diphenylacetyl)-5,6-dimetoxycyclopentao[h]-1,2,3,4-tetrahydroisoquinoline, N-(4-fluorophenylacetyl)-5,6-dimethoxycyclopentano[h]-1,2,3,4-tetrahydroisoquinoline and N-(3,4,5-trimethoxybenzoyl)-5,6-dimethoxy-cyclopentano[h]-1,2,3,4-tetrahydroisoquinoline.

The amides can be readily reduced chemically to the tertiary amine compounds of Formula 2 where $R_4$ has at least 2 carbon atoms. Chemical reduction of the amides can be effected by use of a suitable reducing agent, such as lithium aluminum hydride in anhydrous ether at a temperature which increases the reaction rate, such as the reflux temperature. The resulting tertiary amine can be recovered and isolated as an acid addition salt using standard techniques.

Some of the tertiary amines which can be produced as described are N-ethyl-5,6-dimethoxycyclopentano[h]-1,2,3,4-tetrahydroisoquinoline, N-propyl-5,6-dimethoxycyclopentano[h]-1,2,3,4-tetrahydroisoquinoline, N-phenylethyl-5,6-diethoxycyclopentano[h]-1,2,3,4-tetrahydroisoquinoline, N-benzyl-5,6-dimethoxycyclopentano[h]-1,2,3,4-tetrahydroisoquinoline, N-(3,4-dimethoxybenzyl)-5,6-dimethoxycyclopentano[h]-1,2,3,4-tetrahydroisoquinoline, N-(3,4,5-trimethoxyphenylethyl)-5,6-dimethoxycyclopentano[h]-1,2,3,4-tetrahydroisoquinoline, N-(diphenylethyl)-5,6-dimethoxycyclopentano[h]-1,2,3,4-tetrahydroisoquinoline, N-(4-fluorophenylethyl)-5,6-dimethoxycyclopentano[h]-1,2,3,4-tetrahydroisoquinoline and N-(4-methylbenzyl)-5,6-diethoxycyclopentano[h]-1,2,3,4-tetrahydroisoquinoline.

The compounds of Formula 2 in which $R_4$ is methyl can be prepared by reacting the secondary amines previously named above with formic acid and formaldehyde at an elevated temperature according to the standard procedures for methylating secondary amines to tertiary amines by this process. Some of the tertiary amines which are produced in this way are N-methyl-5,6-dimethoxycyclopentano[h]-1,2,3,4-tetrahydroisoquinoline, N-methyl-5,6-diethoxycyclopentano[h]-1,2,3,4-tetrahydroisoquinoline and N-methyl-5,6-dipropoxycyclopentano[h]-1,2,3,4-tetrahydroisoquinoline.

A second method of making the compounds of Formula 2 is to react the secondary amine starting materials with an appropriate aldehyde to form an intermediate imine or Schiff's base which can then be reduced catalytically with hydrogen at a moderate pressure and moderately elevated temperature. This process can be represented as follows:

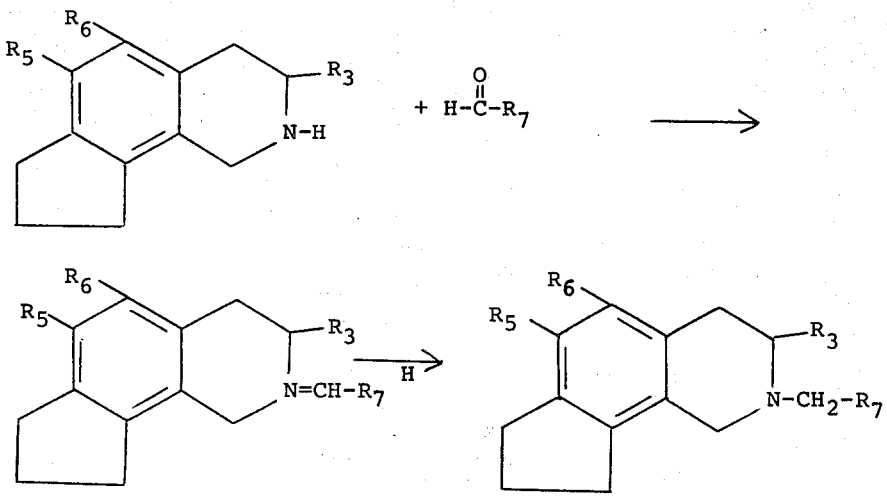

wherein $R_3$, $R_5$, $R_6$ and $R_7$ have the previously assigned significance.

Representative of the aldehydes which can be used in this process are acetaldehyde, propionaldehyde, butyraldehyde, benzaldehyde, 3,4-dimethoxybenzaldehyde, phenylacetaldehyde, diphenylacetaldehyde, p-chlorobenzaldehyde, $\beta,\beta,\beta$-trifluoropropionaldehyde, 3,5-dimethylbenzaldehyde and $\alpha$-phenylpropionaldehyde.

Some of the Schiff's bases or imines which are produced as intermediates in the described process are N-ethylidene-5,6-dimethoxycyclopentano[h]-1,2,3,4-tetrahydroisoquinoline, N-propylidene-5,6-dimethoxycyclopentano[h]-1,2,3,4-tetrahydroisoquinoline, N-benzylidene-5,6-diethoxycyclopentano[h]-1,2,3,4-tetrahydroisoquinoline, N-phenylethylidene-5,6-dipropoxycyclopentano[h]-1,2,3,4-tetrahydroisoquinoline and N-diphenylethylidene-5,6-dimethoxycyclopentano[h]-1,2,3,4-tetrahydoisoquinoline.

Reduction of the intermediate imines can be readily effected by catalytic hydrogenation at moderate pressures using platinum oxide or palladium as the catalyst and a suitable liquid carrier such as glacial acetic acid at room temperature or a moderately elevated temperature such as up to 50°C. Following completion of the hydrogen uptake the reaction mixture can be handled in a conventional way to isolate the desired tertiary amine. Tertiary amines such as those previously named herein can be produced by this process.

The tertiary amines provided by this invention having 5,6-dialkoxy substituents can be converted to the corresponding 5,6-dihydroxy compounds by use of concentrated hydrogen bromide or hydrogen iodide in water or acetic acid solution to cleave the ether linkages. It is preferred to use 48% hydrogen bromide in water for this cleavage. The reaction proceeds readily at an elevated temperature, and preferably the reflux temperature. The process can be represented as follows:

wherein $m$ and $n$ are integers from 0 to 5 and $R_3$ and $R_4$ have the previously assigned significance Some of the compounds which can be produced by cleavage of the alkoxy groups from the 5,6-positions are N-ethyl-5,6-dihydroxycyclopentano[h]-1,2,3,4-tetrahydroisoquinoline, N-propyl-5,6-dihydroxycyclopentano[h]-1,2,3,4-tetrahydroisoquinoline, N-phenylethyl-5,6-dihydroxycyclopentano[h]-1,2,3,4-tetrahydroisoquinoline, N-benzyl-5,6-dihydroxycyclopentano[h]-tetrahydroisoquinoline, N-(3,4-dimethoxybenzyl)-5,6-dihydroxycyclopentano[h]-1,2,3,4-tetrahydroisoquinoline, N-(3,4,5-trimethoxyphenylethyl)-5,6-dihydroxycyclopentano[h]-1,2,3,4-tetrahydroisoquinoline, N-(diphenylethyl)-5,6-dihydroxycyclopentano[h]-1,2,3,4-tetrahydroisoquinoline, N-(4-fluorophenylethyl)-5,6-dihydroxycyclopentao[h]-1,2,3,4-tetrahydroisoquinoline and N-(4-methylbenzyl)-5,6-dihydroxycyclopentano[h]-1,2,3,4-tetrahydroisoquinoline.

The N-substituted -5,6-dihydroxycyclopentano[h]-1,2,3,4-tetrahydroisoquinolines can be converted to esters by reaction with suitable esterifying agents such as alkanoic acid anhydrides, alkanoyl halides, alkanoic acids and aralkanoyl halides. This process can be represented as follows:

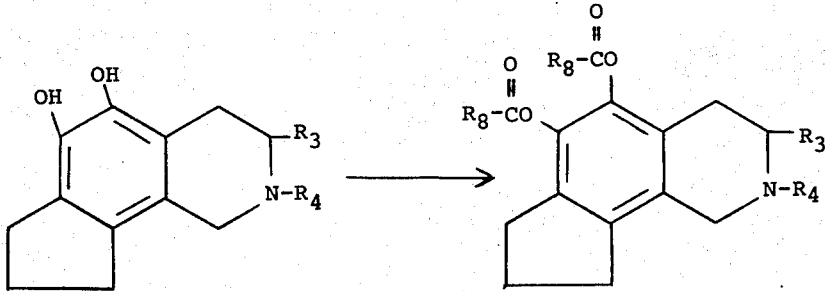

wherein $R_3$ and $R_4$ have the previously assigned significance and $R_8$ is a lower alkyl or aryl-lower alkyl group.

Conventional methods can be used to prepare and isolate the esters. Some of the esters which can be produced from the otherwise corresponding 5,6-dihydroxy compounds are N-methyl-5,6-diacetoxycyclopentano[h]-1,2,3,4-tetrahydroisoquinoline, N-propyl-5,6-dipropionyloxycyclopentano[h]-1,2,3,4-tetrahydroisoquinoline, N-benzyl-5,6-dibenzoyloxycyclopentano[h]-1,2,3,4-tetrahydroisoquinoline and N-diphenylethyl-5,6-diphenylacetoxycyclopentano[h]-1,2,3,4-tetrahydroisoquinoline.

The tertiary amines of this invention can be converted to acid addition salts by contacting the amines with a suitable inorganic acid such as hydrochloric

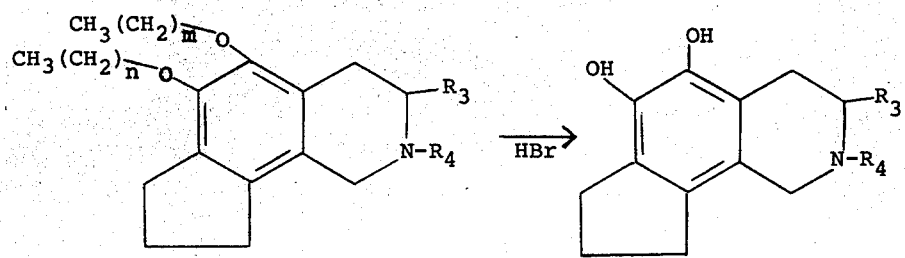

acid, sulfuric acid, phosphoric acid and hydrobromic acid or an organic acid such as citric acid, acetic acid, formic acid, malic acid, fumaric acid, succinic acid, benzoic acid and tartaric acid.

Quaternary ammonium salts of the compounds are readily prepared by contacting the compounds with an alkyl halide or an alkyl sulfate, aralkyl halide or arakyl sulfate such as methyl chloride, ethyl bromide, propyl iodide, benzyl chloride, benzyl sulfate and methyl sulfate as well as other compounds known to form quaternary ammonium salts with tertiary amines.

The tertiary amines of this invention are useful as neutralizing agents since they are bases which form salts with acids.

According to a second aspect of the invention, the compounds are also useful pharmaceutically. These compounds as the base or acid addition salt when administered to animals parenterally or orally exert an anti-hypertensive effect. The compounds thus can be used to reduce blood pressure.

N-methyl-5,6-dihydroxycyclopentano[h]-1,2,3,4-tetrahydroisoquinoline has an $ALD_{50}$ in mice of 160–200 mg/kg i.p. When administered at 50 mg/kg i.p. to hypertensive rats the following percent change in systolic blood pressure was observed:

| | |
|---|---|
| 1 hour | $-9.1 \pm 2.7$ |
| 2 hours | $-3.5 \pm 2.4$ |
| 4 hours | $-5.7 \pm 3.3$ |
| 24 hours | $-3.7 \pm 3.0$ |

In the anesthetized normotensive dog a dose of 5 mg/kg i.v. in saline lowered blood pressure 11% and after 33 minutes there was 50% return to normal blood pressure.

N-(2-methylbutyl)-5,6-dimethoxycyclopentano[h]-1,2,3,4-tetrahydroisoquinoline has an $ALD_{50}$ in mice of 178–200 mg/kg i.p. when administered in water. When administered at 25 mg/kg i.p. in water to hypertensive rats the following percent change in systolic blood pressure was observed:

| | |
|---|---|
| 1 hour | $-17.2 \pm 4.8$ |
| 2 hours | $-12.6 \pm 4.4$ |
| 4 hours | $-6.7 \pm 5.3$ |
| 24 hours | $+1.3 \pm 5.0$ |

N-(3,4-dimethoxybenzoyl)-5,6-dimethoxycyclopentano[h]-1,2,3,4-tetrahydroisoquinoline has an $ALD_{50}$ greater than 1000 mg/kg i.p. when adminstered to mice as a suspension in 1% tragacanth. When administered at 100 mg/kg i.p. as a suspension in 1% tragacanth to hypertensive rats the following percent change in systolic blood pressure was observed:

| | |
|---|---|
| 1 hour | $-12.1 \pm 2.2$ |
| 2 hours | $-8.8 \pm 2.2$ |
| 4 hours | $-3.4 \pm 1.5$ |
| 24 hours | $-6.0 \pm 2.0$ |

In the anesthetized normotensive dog a dose of 5 mg/kg i.v. administered in polyethylene glycol lowered blood pressure 34% and after 1 minute there was a 50% return to normal blood pressure.

N-(3,4-dimethoxybenzyl)-5,6-dimethoxycyclopentano[h]-1,2,3,4-tetrahydroisoquinoline has an $ALD_{50}$ of 200–250 mg/kg i.p. in mice as a suspension in 1% tragacanth. When administered at 50 mg/kg i.p. as a suspension in 1% tragacanth to hypertensive rats the following percent change in systolic blood pressure was observed:

| | |
|---|---|
| 1 hour | $-8.4 \pm 2.8$ |
| 2 hours | $-2.4 \pm 4.1$ |
| 4 hours | $-1.0 \pm 1.1$ |
| 24 hours | $+3.3 \pm 2.4$ |

The amount of active ingredient administered may be varied; however, it is necessary that the amount of active ingredient be such that a suitable dosage is given. The selected dosage depends upon the desired therapeutic effect and on the duration of treatment. Dosages of from 0.1 to 25 mg/kg of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmacuetical carriers which are liquid or solid can be used. Solid carriers such as starch, sugar, talc and the like can be used to form powders. The powders can be used for direct administered or they may be used to make tablets or to fill gelatin capsules. Suitable lubricants like magnesium stearate, binders such as gelatin, and distintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg of active agent.

A typical tablet can have the composition:

| | Mg |
|---|---|
| Active agent (1) | 100 |
| Starch U.S.P. | 57 |
| Lactose U.S.P. | 73 |
| Talc. U.S.P. | 9 |
| Stearic acid | 12 |

(1) N-methyl-5,6-dihydroxycyclopentano[h]-1,2,3,4-tetrahydroisoquinoline.

The compounds exhibit both oral and parenteral activity and accordingly they can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

THE PREPARATION OF STARTING MATERIALS USED IN THIS INVENTION

Intermediate indanaldehydes of the following formula are first prepared:

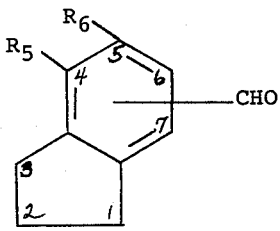

in which the —CHO is in the 6 or 7-position and $R_5$ and $R_6$ have the previously assigned meaning. These compounds are prepared by reducing a 4,5-dialkoxy-1-indanone to 4,5-dialkoxyindane and then converting that compound by means of a Friedel-Crafts reaction to a mixture of 4,5-dialkoxy-6-indanaldehyde and 4,5-dialkoxy-7-indanaldehyde. This series of reactions can be represented as follows:

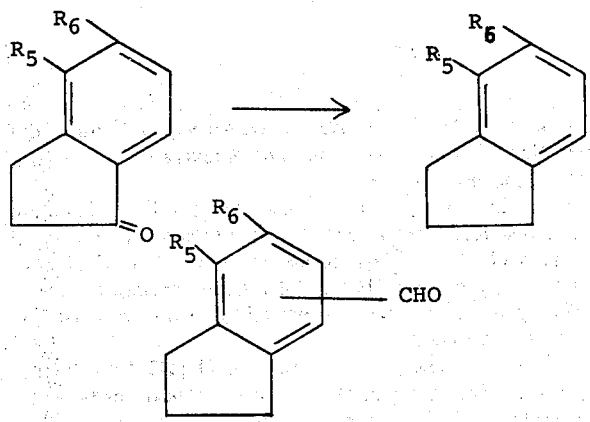

wherein $R_5$ and $R_6$ have the previously assigned significance.

Among the starting materials which can be used in the described sequence of reactions are 4,5-dimethoxy-1-indanone, 4,5-diethoxy-1-indanone, 4,5-dipropoxy-1-indanone and 4-methoxy-5-ethoxy-1-indanone. The publication of John Koo in J. Am. Chem. Soc., 75, 1891 (1953) discloses 4,5- dimethoxy-1-indanone. Other similar compounds, such as those just named, can be prepared by the procedure disclosed therein.

Reduction of the 4,5-dialkoxy-1-indanone can be readily achieved catalytically using hydrogen and a suitable catalyst such as palladium. The hydrogenation is effected by placing the starting material in glacial acetic acid containing the catalyst and a small amount of concentrated hydrochloric acid. The hydrogenation proceeds readily at room temperature using a hydrogen pressure of about 25 to 100 psig. After hydrogen uptake has ceased the product can be recovered from the reaction mixture by conventional methods.

Some 4,5-dialkoxyindanes which can be produced as described are 4,5-dimethoxyindane, 4,5-diethoxyindane, 4,5-dipropoxyindane, 4,5-diisopropoxyindane, 4,5-dibutoxyindane and 4-methoxy-5-ethoxyindane.

Formylation of a 4,5-dialkoxyindane according to the method of Alfred Rieche et al. in Chem. Ber., 93, 88 (1960) using a Friedel-Crafts catalyst such as stannic tetrachloride, aluminum trichloride or titanium tetrachloride and $\alpha,\alpha$-dichloromethyl methyl ether followed by water leads to the production of a mixture containing 4,5-dialkoxy-6-indanaldehyde and 4,5-dialkoxy-7-indanaldehyde. The presence of a mixture of isomeric aldehydes is shown by gas-liquid chromatography. A mixture of 4,5-dimethoxy-6- and -7- indanaldehydes formed by the described procedure contains about 75% of the 7-formyl and 25% of the 6-formyl isomers. Obviously, the presence of other alkoxy groups than the methoxy group could lead to different amounts of the isomers in the relating mixture.

The isomeric mixture of aldehydes obtained by the described process is generally a liquid. Residual amounts of solvent are removed from the liquid by distillation following which the product is distilled under high vacuum to give a pure liquid mixture. Upon cooling, one of the isomeric aldehydes crystallizes from the liquid and is removed by filtration. Thus, 4,5-dimethoxy-7-indanaldehyde crystallizes and leaves a liquid which is primarily 4,5-dimethoxy-6-indanaldehyde.

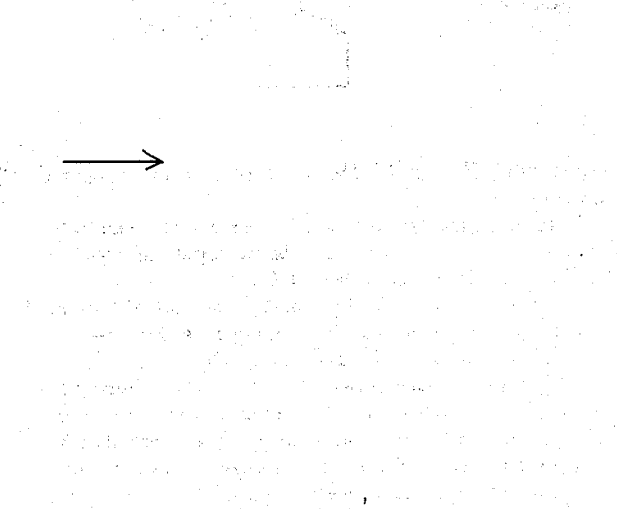

Fractional distillation of the liquid gives the pure 6-formyl isomer.

Some of the separated purified aldehydes which can be prepared by the described method are:
4,5-dimethoxy-6-indanaldehyde,
4,5-diethoxy-6-indanaldehyde,
4,5-dipropoxy-6-indanaldehyde,
4,5-dibutoxy-6-indanaldehyde, and
4-methoxy-5-ethoxy-6-indanaldehyde.

The 5,6-dialkoxy-cyclopentano[h]1,2,3,4-tetrahydroisoquinolines used as starting materials are prepared from 4,5-dialkoxy-6-indanaldehydes by reacting the aldehyde with a 1-nitroalkane to produce a 4,5-dialkoxy-6-nitrovinylindane, chemically reducing the nitrovinyl compound to the corresponding aminoalkyl compound, reacting the resulting amine with formaldehyde to produce a Schiff's base and then treating the Schiff's base with acid to effect a Pictet-Spengler acid catalyzed ring closure. This series of reactions can be represented as follows:

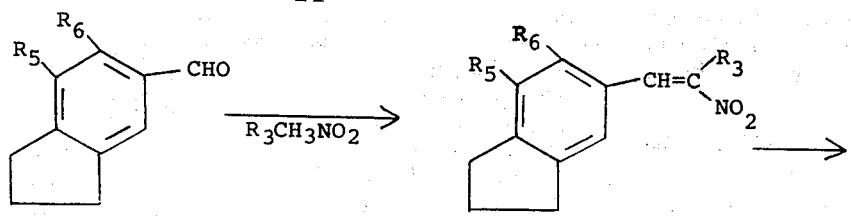

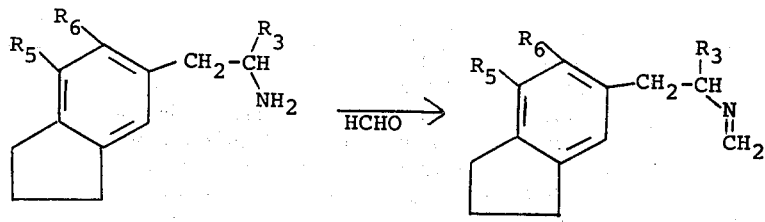

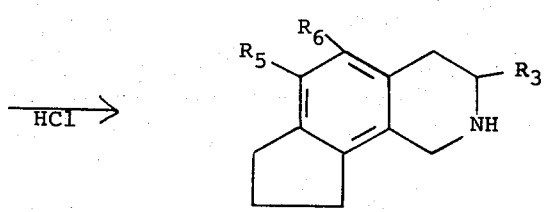

wherein $R_3$, $R_5$ and $R_6$ have the previously assigned meaning.

In effecting the first step of this series of reactions, nitromethane, nitroethane, 1-nitropropane and other such 1-nitroalkanes can be used.

Condensation of the 4,5-dialkoxy-6-indanaldehyde with the nitroalkane can be readily effected by procedures disclosed in Gairaud et al., J. Org. Chem., 18, 1 (1953) and particularly by the use of ammonium acetate in glacial acetic acid at an elevated temperature. After cooling the reaction mixture, the desired 4,5-dialkoxy-6-nitrovinylindane crystallizes from solution and is separated by filtration.

By following the described procedure there is obtained 4,5-dimethoxy-6-nitrovinylindane, 4,5-dimethoxy-6-(2-nitro-2-methylvinyl)indane, 4,5-dimethoxy-6-(2-nitro-2-ethylvinyl)indane, 4,5-diethoxy-6-nitrovinylindane, 4,5-dipropoxy-6-nitrovinylindane and 4-methoxy-5-ethoxy-6-nitrovinylindane.

The 4,5-dialkoxy-6-nitrovinylindanes are readily reduced chemically by means of lithium aluminum hydride in dry ether according to the method of Marchant et al., J. Chem. Soc., 327 (1956) to produce the desired 4,5-dialkoxy-6-aminoethylindanes. Some of the compounds which are produced in this way are 4,5-dimethoxy-6-aminoethylindane, 4,5-diethoxy-6-(2-aminopropyl)indane, 4,5-dipropoxy-6-(2-aminobutyl)indane and 4-methoxy-5-ethoxy-6-aminoethylindane.

The 4,5-dialkoxy-6-aminoethylindanes are converted to the Schiff's bases by reaction with formaldehyde using conventional reaction conditions for preparing Schiff's bases. some of the compounds so produced are N-methylidene-4,5-dimethoxy-6-(2-aminoethyl)indane, N-methylidene-4,5-diethoxy-6-(2-aminopropyl-)indane, N-methylidene-4,5-dipropoxy-6-(2-aminobutyl)indane and N-methylidene-4-methoxy-5-ethoxy-6-(2-aminoethyl)indane.

The described Schiff's bases are readily cyclized in aqueous acid, such as 23% hydrochloric acid, at a moderately elevated temperature of about 40° to 75°C., to the cyclopentano[h]1,2,3,4-tetrahydroisoquinolines. The product is readily recovered by evaporation of the solvent and acid.

Representative cyclopentano[h]1,2,3,4-tetrahydroisoquinolines which are produced as described are 5,6-dimethoxy-cyclopentano[h]1,2,3,4-tetrahydroisoquinoline, 5,6-diethoxy-cyclopentano[h]1,2,3,4-tetrahydroisoquinoline, 5,6-dipropoxy-cyclopentano[h]1,2,3,4-tetrahydroisoquinoline and 5-methoxy-6-ethoxy-cyclopentano[h]1,2,3,4-tetrahydroisoquinoline.

The following Examples 1 to 10 are presented to illustrate the preparation of compounds within the invention.

EXAMPLE 1

N-Methyl-5,6-dimethoxycyclopentano[h]-1,2,3,4-tetrahydroisoquinoline hydrobromide In 16 ml of formic acid and 10 ml of formalin, 4.659 g (0.020 mole) of 5,6-dimethoxycyclopentano[h]-1,2,3,4-tetrahydroisoquinoline was refluxed for 6 hrs. and stirred over a weekend. After pouring the reaction mixture into ice, 25 g of sodium hydroxide in water at 5°C. was added and the precipitate formed was extracted with ether. Removal of the solvent gave 4.86 g of a yellow oil which was dissolved in anhydrous ether and treated with a solution off hydrogen bromide gas in ether. The precipitated salt was filtered and dried in a vacuum oven giving 6.25 g of a white powder. From ethanol-ether solution 2.0 g of this material was recrystallized twice to give 0.95 g (45%), m.p. 133°–136°C.

Anal. Calcd. for $C_{15}H_{22}BrNO_2$: C, 54.88; H, 6.75; N, 4.26; Br, 24.34. Found: C, 54.78; H, 6.75; N, 4.34; Br, 24.33.

EXAMPLE 2

N-Methyl-5,6-dihydroxycyclopentano[h]-1,2,3,4-tetrahydroisoquinoline hydrobromide Following reflux of 2.0 g (0.0061 mole) of N-methyl-5,6-dimethoxycyclopentano[h]-1,2,3,4-tetrahydroisoquinoline HBr in 20 ml of 48% HBr for 2 hrs., the water-acid solvent was removed on a rotary evaporator and the remaining solid was dried in a vacuum oven in the presence of $P_2O_5$. The salt was found to crystallize from water but water proved not to be suitable for purification. Finally recrystallization from acetonitrile-absolute ethanol gave 1.302 g (71%) of shiny needles, m.p. 276.5°–278°C.

Anal. Calcd. for $C_{13}H_{18}NO_2Br$: C, 52.01; H, 6.04; N, 4.66; Br, 26.61. Found: C, 52.11; H, 5.97; N, 4.71; Br, 26.46.

EXAMPLE 3

N-(2,2-Diphenylethyl)-5,6-dimethoxycyclopentano[h]-1,2,3,4-tetrahydroisoquinoline After refluxing 2.52 g (0.011 mole) of 5,6-dimethoxycyclopentano[h]-1,2,3,4-tetrahydroisoquinoline and 4.24 g (0.028 mole) if diphenylacetaldehyde in 150 ml of benzene for about 24 hrs., the solvent was removed on a rotary evaporator. The oil thus obtained was dissolved in 30 ml of glacial acetic acid and hydrogenated over 0.5 g of Pd/C at 40 psi for 48 hrs. After removing the catalyst and rinsing with methanol, the solvents were removed on a rotary evaporator. The remaining oil was dissolved in methanol and treated with cold sodium hydroxide solution giving a precipitate which was extracted with ether. An nmr spectrum of the material obtained after distillation of the ether indicated incomplete hydrogenation. Hydrogenation was repeated as before using 0.5 g of $PtO_2$ as catalyst rather than Pd/C. The oil obtained from this reaction showed hydroxyl absorption in the ir and probably contained some diphenylethanol. A hydrobromide salt was made in anhydrous ether giving 3.02 g of a tan powder. After dissolving the salt in methanol, precipitating the amine with sodium hydroxide solution and extracting the amine with ether, the solvent was removed and the resulting oil was crystallized from absolute ethanol giving 1.351 g (30%) of the desired amine, m.p. 116.5°–118°C.

Anal. Calcd. for $C_{28}H_{13}NO_2$: C, 81.32; H, 7.55; N, 3.38. Found: C, 81.43; H, 7.38; N, 3.31.

EXAMPLE 4

N-(2-Methylbutyl)-5,6-dimethoxycyclopentano[h]-1,2,3,4-tetrahydroisoquinoline hydrobromide In 70 ml of benzene 2.26 g (0.0096 mole) of 5,6-dimethoxycyclopentano[h]-1,2,3,4-tetrahydroisoquinoline, 1.20 g (0.0099 mole) of α-methylbutyrylchloride and 5–6 ml of triethylamine were refluxed for 30 hrs. After cooling and pouring the reaction mixture into a separatory funnel, it was washed with water, 10% hydrochloric acid, 5% sodium hydroxide and again with water. The solvent was thoroughly removed on a rotary evaporator giving 2.91 g of the amide which, after thorough drying, was reduced in 250 ml of isopropyl ether and 60 ml of anhydrous ether by 1.0 g (0.026 mole) of $LiAlH_4$ with refluxing for 48 hrs. To this mixture 5.0 g of a filter aid and 5–10 ml of water was added slowly dropwise with cooling in an ice bath followed by filtration of the white salts, washing with ether and evaporation of the solvent on a rotary evaporator giving 2.64 g of a lightly colored oil. The hydrobromide salt was made in the usual way by precipitating the amine from ether by slow addition of hydrogen bromide gas dissolved in dry ether. After collecting a powder by filtration and drying, the powder was dissolved in excess ethylacetate, boiled with activated charcoal, filtered and then the volume of the solven was reduced causing the product to crystallize. From this, 1.768 g (47%) of the salt was obtained, m.p. 156.5°–158°C.

Anal. Calcd. for $C_{19}H_{30}BrNO_2$: C, 59.37; H, 7.86; N, 3.64; Br, 20.78. Found: C, 59.24; H, 7.94; N, 3.69; Br, 20.91.

EXAMPLE 5

N-(3,4-Dimethoxybenzoyl)-5,6-dimethoxycyclopentano [h]-1,2,3,4-tetrahydroisoquinoline A solution of 2.00 g (0.0086 mole) of 5,6-dimethoxycyclopentano[h]-1,2,3,4-tetrahydroisoquinoline, 5–6 ml of triethylamine and 1.72 g (0.0086 mole) of 3,4-dimethoxybenzoyl chloride in benzene were refluxed 24 hrs. After cooling, the reaction mixture was poured into a separatory funnel and washed with water, 10% hydrochloric acid, 12% sodium hydroxide, water and the solvent was thoroughly removed on a rotary evaporator giving 3.60 g of an oil which was purified by column chromatography on silica gel. The compound was eluted with 500 ml of benzene, 200 ml of 75:25 benzene:chloroform, 1100 ml of 50:50 benzene: chloroform and 800 ml of 25:75 benzene:chloroform. The material which came off the column in the 50:50 chloroform:benzene fraction was combined, boiled with activated charcoal in 90°–120°C. ligroine, filtered, and reduced in volume. The amide crystallized as a powder. Another recrystallization gave 1.253 g (39%) of white powder, m.p. 106°–108° C.

Anal. Calcd. for $C_{23}H_{27}NO_5$: C, 69.50; H, 6.84; N, 3.52. Found: C, 69.59; H, 6.91; N, 3.45.

EXAMPLE 6

N-(3,4-Dimethoxybenzyl)-5,6-dimethoxycyclopentano [h]-1,2,3,4-tetrahydroisoquinoline hydrobromide A solution of 1.056 g (0.0026 mole) of N-(3,4-dimethoxybenzoyl)-5,6-dimethoxycyclopentano[h]-1,2,3,4-tetrahydroisoquinoline and 1.0 g (0.026 mole) of $LiAlH_4$ was refluxed for about 48 hrs. After cooling and adding 5.0 g of filter aid followed by 8 ml of water added dropwise with caution, the ether was decanted and the white salts washed with ether followed by decantation and filtration. Removal of the solvent gave 0.86 g of colorless oil. The hydrobromide salt was formed as described in Example 4. The solid, white salt was pure without further treatment giving 0.84 g (68%) of material, m.p. 226°–228.5°C.

Anal. Calcd. for $C_{23}H_{30}NO_4Br$: C, 59.48; H, 6.51; N, 3.01; Br, 17.20; Found: C, 59.34; H, 6.45; N, 2.99; Br, 17.11.

EXAMPLE 7

N-(3,4-Dimethoxyphenylacetyl)-5,6-dimethoxycyclopentano[h]-1,2,3,4-tetrahydroisoquinoline In 70 ml of benzene 1.5 g (0.0064 mole) of 5,6-dimethoxycyclopentano[h]-1,2,3,4-tetrahydroisoquinoline, 1.38 g (0.0064 mole) of 3,4-dimethoxyphenylacetyl chloride (distilled carefully under high vacuum just before use) and 2 ml of triethylamine were refluxed for 20 hrs. The reaction mixture was cooled, poured into a separatory funnel and washed with water, 2 × 100 ml of 10% hydrochloric acid, 2 × 100 ml of 8% sodium hydroxide and 2 × 150 ml of water. After drying the solution over anhydrous sodium sulfate and carefully removing the solvent on a rotary evaporator a viscous oil was obtaned which did not crystallize from ligroine. Column chromatography of 1.0 g of this substance on slica gel as described in Example 5 gave a pure fraction (from the 50:50 benzene:chloroform eluent) which crystallized; 310 mg (11%), m.p. 101°–102°C.

Anal. Calcd. for $C_{24}H_{29}NO_5$: C, 70.05; H, 7.10; N, 3.40. Found: C, 70.27; H, 7.22; N, 3.36.

EXAMPLE 8

N-(3,4-Dimethoxyphenylethyl)-5,6-dimethoxycyclopentano[h]-1,2,3,4-tetrahydroisoquinoline hydrobromide To 1.0 g (0.026 mole) of LiAlH$_4$ stirred in anhydrous ether was added slowly 1.0 g (0.0024 mole) of N-(3,4-dimethoxyphenylacetyl)-5,6-dimethoxycyclopentano[h]-1,2,3,4-tetrahydroisoquinoline in anhydrous ether. Refluxing was continued about 20 hrs. After decomposing excess LiAlH$_4$ as described in Example 6, removing the solvent and drying the remaining oil, the oil was dissolved in ether and a solution of hydrogen bromide gas in anhydrous ether was slowly added until no further precipitate was obtained. The product was recrystallized twice from acetonitrile giving 262 mg of the hydrobromide, m.p. 235°–236°C.

Anal. Calcd. for $C_{24}H_{32}NO_4Br$: C, 60.25; H, 6.74; N, 2.92; Br, 16.70. Found: C, 60.31; H, 6.78; N, 2.87; Br, 16.61.

EXAMPLE 9

N-(Diphenylacetyl)-5,6-dimethoxycyclopentano[h]-1,2,3,4-tetrahydroisoquinoline In 50 ml of dry benzene, 1.50 g (0.0064 mole) of 5,6-dimethoxycyclopentano[h]-1,2,3,4-tetrahydroisoquinoline, 1.48 g (0.0064 mole) of diphenylacetylchloride (freshly distilled) and 2 ml of triethylamine were refluxed about 21 hrs. After cooling, the contents of the reaction flask were rinsed into a separatory funnel with benzene and washed with water, 2 × 100 ml of 10% hydrochloric acid (v/v), 2 × 100 ml of 8% sodium hydroxide and then water. The remaining benzene solution was dried over sodium sulfate and then the solvent was removed giving a lightly colored viscous oil which weighed 2.37 g. This oil was chromatographed on a silica gel column under the same conditions as described in Example 5 giving 1.629 g (591%) of the desired amide as a viscous oil.

Anal. Calcd. for $C_{28}H_{29}NO_3$: C, 78.66; H, 6.83; N, 3.27. Found: C, 78.64; H, 6.79; N, 3.17.

EXAMPLE 10

N-Methyl-5,6-diacetoxycyclopentano[h]-1,2,3,4-tetrahydroisoquinoline

In 27.0 g of trifluoroacetic anhydride and 7.5 g (0.170 mole) of glacial acetic acid, 1.5 g (0.005 mole) of N-methyl-5,6-dihydroxycyclopentano[h]-1,2,3,4-tetrahydroisoquinoline HBr was refluxed overnight. After cooling, the solvent and reactants were removed on a rotary evaporator giving an oil which weighed 2.7 g. Prolonged stirring of the oil under anhydrous ether gave a tan powder (0.92 g.) which did not recrystallize from any solvents tried. Therefore, this material was dissolved in ethanol and precipitated by addition of 8% NaHCO$_3$ solution and water. The pecipitate was extracted with ether and the ether was evaporated giving an oil which solidified. The solid was recrystallized twice from 90–120°C. ligroine yielding 176 mg (12%) of slightly orange prisms, m.p. 127°–128.5°C.

Anal. Calcd. for $C_{17}H_{21}NO_4$: C, 67.30; H, 6.97; N, 4.61. Found: C, 67.35; H, 7.03; N, 4.54.

The following examples are presented to illustrate the preparation of compounds used as starting materials in the invention.

EXAMPLE 11

4,5-Dimethoxyindane

A mixture of 52.6 g (0.275 mole) of 4,5-dimethoxy-1-indanone, 3.00 g of 5% Pd/C, 100 ml of glacial acetic acid and 20 drops of conc. HCl was hydrogenated at 45 psi and room temperature until hydrogen uptake ceased. Following filtration of the used catalyst, two methods were used to work up the reaction.

A. The acid was neutralized with dilute sodium hydroxide and the product extracted from the aqueous phase with ether. The other was removed by distillation and crude 4,5-dimethoxyindane was distilled under reduced pressure, b.p. 133°–135°C (15 mm) yielding 42.0 g (86.4%) of clear liquid. Infrared analysis showed the absence of carbonyl absorption.

B. Most of the acetic acid was removed on a rotary evaporator and the remaining liquid was distilled as before giving 4,5-dimethoxyindane with no significant difference in yield from that obtained in A.

EXAMPLE 12

4,5-Dimethoxy-6-indanaldehyde

To a solution of 10.0 g (0.056 mole) of 4,5-dimethoxyindane, 24.0 g (0.126 mole) of titanium tetrachloride and 104 ml of CH$_2$Cl$_2$ in a 250 ml 3-necked flask fitted with a thermometer and condenser and magnetically stirred, 11.0 g (0.096 mole) of α,α-dichloromethyl methyl ether was added rapidly dropwise at 0°C. Hydrogen chloride gas was liberated during the course of the reaction. After vigorous evolution of HCl had subsided, the reaction solution was allowed to slowly warm to room temperature and it was stirred for 1 to 2 hours. The solution was refluxed for 6 hours, cooled and the reaction mixture was poured over 200 ml of ice and water (ether and salt were added at this point to increase the volume of the organic phase, to invert the two layers and to break emulsions). The organic phase was washed with 2 × 100 ml of 8% NaHCO$_3$ solution, 1 × 100 ml of water and dried over Na$_2$SO$_4$. After removal of the solvent by distillation, the mixture of aldehyde isomers was distilled under high vacuum (b.p. 115°–126°C; 0.28 mm) giving 10.2 g of the 6- and 7-position aldehydes (88%). The 7-position aldehyde which crystallized from the liquid was filtered. This process was repeated several times by seeding the filtrate followed by cooling.

The 4,5-dimethoxy-6-indanaldehyde was obtained by high vacuum (20–50μ) fractional distillation of the mixture of aldehydes remaining after repeated crystallization and filtering off of the 7-aldehyde. The 6-aldehyde distilled as a pure substance in the first fractions followed by a mixture of the aldehydes and finally the pure 7-aldehyde. The 4,5-dimethoxy-6-indanaldehyde was a liquid at room temperature but crystallized when refrigerated. An approximate m.p. (11°C) was obtained from the temperature of a mixture of the solid in equilibrium with the liquid.

Anal. Calcd. for $C_{12}H_{14}O_3$: C, 69.88; H, 6.84. Found: C, 70.13; H, 6.87.

EXAMPLE 13

4,5-Dimethoxy-6-nitrovinylindane

In a 2 liter 3-necked flask fitted with a condenser and thermometer and magnetically stirred, 126.7 g (0.613 mole) of 4,5-dimethoxy-6-indanaldehyde, 29.3 g (0.380 mole) of ammonium acetate, 127 ml (2.82 mole) of nitromethane and 390 ml of acetic acid were heated at 112°C for 45 minutes. After cooling in the refrigerator and scratching with a glass rod the solution crystallized. After filtering and washing with cold acetic acid the product was dried under vacuum overnight and recrystallized from methanol yielding 104.4 g (68%) of 4,5-dimethoxy-6-nitrovinylindane as yellow needles, m.p. 103.5°–104.5°C.

Anal. Calcd. for $C_{13}H_{15}NO_4$: C, 62.64; H, 6.06; N, 5.62. Found: C, 62.45; H, 6.17; N, 5.84.

EXAMPLE 14

4,5-Dimethoxy-6-aminoethylindane

To 9.2 g (0.242 mole) $LiAlH_4$ in 400 ml of anhydrous ether was added 12.17 g (0.048 mole) of 4,5-dimethoxy-6-nitrovinylindane in 1 liter of anhydrous ether dropwise over a period of 4 hours while refluxing; this was followed by refluxing for a further 2 hours. After adding 15 g of diatomaceous earth and decomposing excess $LiAlH_4$ with 40 ml of $H_2O$ (while cooling in an ice bath), the ether was decanted and the salts were washed twice with ether followed by decantation and finally filtering. The ether was removed by distillation and the 4,5-dimethoxy-6-aminoethylindane was distilled yielding 7.42 g (68%), b.p. 101°–103°C (75μ).

Anal. Calcd. for $C_{13}H_{19}NO_2$: C, 70.55; H, 8.65; N, 6.32. Found: C, 70.68; H, 8.71; N, 6.35.

EXAMPLE 15

5,6-Dimethoxy-cyclopentano[h]1,2,3,4-tetrahydroisoquinoline hydrochloride

To 7.42 ml of boiling formalin in a 100 ml flask was added dropwise 7.42 g (0.033 mole) of 4,5-dimethoxy-6-aminoethylindane in 15 ml of methanol with magnetic stirring and warming. After heating at 70°–75°C for 45 minutes, the mixture was rinsed into a separatory funnel with 3 × 50 ml of benzene. The benzene layer was washed with 3 × 100 ml of water and then the benzene was thoroughly removed on the evaporator. The ir spectrum showed absence of NH stretching and weakening of intensity of the band at 1576 $cm^{-1}$. The N-methylidene-4,5-dimethoxy-6-(2-aminoethyl)indane weighed 8.72 g and was dissolved in 39 ml of 23% HCl followed by heating at 50°–60°C for 30 minutes. The aqueous acid was removed on a rotary evaporator yielding an oily, viscous substance which was dried in a vacuum oven in the presence of $P_2O_5$. A tacky hygroscopic solid was obtained which was crystallized from ether-ethanol giving fine needles, m.p. 215.5°–216.5°C. Further experimentation showed acetonitrile-ethanol to be a better recrystallization solvent.

Anal. Calcd. for $C_{14}H_{20}NO_2Cl$: C, 62.33; H, 7.47; N, 5.19; Cl, 13.14. Found: C, 62.47; H, 7.33; N, 5.15; Cl, 13.36.

The foregoing detailed description has been given for clearness of understanding only, and no unnecessary limitations should be understood therefrom, as modifications will be obvious to those skilled in the art.

What is claimed is:

1. A compound of the formula

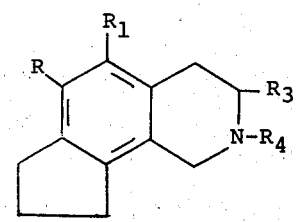

wherein R and $R_1$ represent hydroxy, alkoxy groups having 1 to 8 carbon atoms, alkanoyloxy groups having 1 to 8 carbon atoms, or phenyl-lower alkanoyloxy groups, $R_3$ represents hydrogen, a normal alkyl having 1 to 8 carbon atoms, isopropyl, sec-butyl or isopentyl, and $R_4$ represents alkyl having 1 to 8 carbon atoms, phenyl-carbonyl, phenyl-alkyl, benzyhydryl-alkyl, alkanoyl, phenyl-alkanoyl, benzhydryl-alkanoyl or benzhydrylcarbonyl groups in which groups represented by $R_4$ the alkyl and alkanoyl groups have 1 to 8 carbon atoms, and nontoxic acid addition salts thereof.

2. A compound of the formula

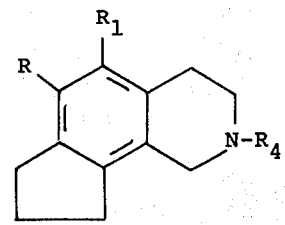

wherein R and $R_1$ represent hydroxy, the same alkoxy groups having 1 to 8 carbon atoms, or the same alkanoyloxy groups having 1 to 8 carbon atoms, and $R_4$ represents alkyl having 1 to 8 carbon atoms, phenyl-carbonyl, phenyl-alkyl, benzhydrylalkyl, alkanoyl, phenyl-alkanoyl, benzhydryl-alkanoyl or benzhydrylcarbonyl groups in which groups represented by $R_4$ the alkyl and alkanoyl groups have 1 to 8 carbon atoms, and nontoxic acid addition salts thereof.

3. A compound of the formula

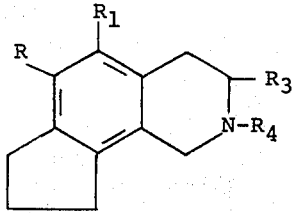

wherein R and $R_1$ represent hydroxy, alkoxy groups having 1 to 8 carbon atoms, alkanoyloxy groups having 1 to 8 carbon atoms, or phenyl-lower alkanoyloxy groups in which the phenyl is unsubstituted or is substituted with one to three nuclear alkoxy groups having 1 to 8 carbon atoms, alkyl groups having 1 to 8 carbon atoms, chloro, bromo, fluoro, hydroxy and amino groups, $R_3$ represents hydrogen, a normal alkyl group having 1 to 8 carbon atoms, isopropyl, sec-butyl or isopentyl, and $R_4$ represents alkyl having 1 to 8 carbon atoms, phenyl-carbonyl, phenyl-alkyl, benzhydryl-alkyl, alkanoyl, phenyl-alkanoyl, benzhydryl-alkanoyl or benzhydrylcarbonyl groups in which groups represented by $R_4$ the alkyl and alkanoyl groups have 1 to 8 carbon atoms and the phenyl and benzhydryl moieties are either unsubstituted or are substituted with one to three nuclear alkoxy groups having 1 to 8 carbon atoms, alkyl groups having 1 to 8 carbon atoms, chloro, bromo, fluoro, hydroxy and amino groups, and non-toxic acid addition salts thereof.

4. A compound according to claim 2 in which R and $R_1$ are each the same alkoxy group, and $R_4$ is an alkyl group.

5. A compound according to claim 2 in which R and $R_1$ are each the same alkoxy group, and $R_4$ is a phenyl-alkyl group.

6. A compound according to claim 2 in which R and $R_1$ are each the same alkoxy group, and $R_4$ is a benzhydryl-alkyl group.

7. A compound according to claim 2 in which R and $R_1$ are each the same alkoxy group, and $R_4$ is an alkanoyl group.

8. A compound according to claim 2 in which R and $R_1$ are each the same alkoxy group, and $R_4$ is a benzhydryl-alkanoyl group.

9. A compound according to claim 2 in which R and $R_1$ are each the same alkoxy group, and $R_4$ is a benzhydrylcarbonyl group.

10. A compound according to claim 2 in which R and $R_1$ are each the same alkoxy group, and $R_4$ is a benzoyl group.

11. A compound according to claim 2 in which R and $R_1$ are each hydroxy, and $R_4$ is an alkyl group.

12. A compound according to claim 2 in which R and $R_1$ are each an alkanoyloxy group, and $R_4$ is an alkyl group.

13. A compound according to claim 4 named N-methyl-5,6-dimethoxycyclopentano-1,2,3,4-tetrahydroisoquinoline.

14. A compound according to claim 11 named N-methyl-5,6-dihydroxycyclopentano-1,2,3,4-tetrahydroisoquinoline.

15. A compound according to claim 6 named N-(2,2-diphenylethyl)-5,6-dimethoxycyclopentano-1,2,3,4-tetrahydroisoquinoline.

16. A compound according to claim 4 named N-(2-methylbutyl)-5,6-dimethoxycyclopentano-1,2,3,4-tetrahydroisoquinoline.

17. A compound according to claim 3 named N-(3,4-dimethoxybenzoyl)-5,6-dimethoxycyclopentano-1,2,3,4-tetrahydroisoquinoline.

18. A compound according to claim 3 named N-(3,4-dimethoxybenzyl)-5,6-dimethoxycyclopentano-1,2,3,4-tetrahydroisoquinoline.

19. A compound according to claim 2 in which R and $R_1$ are each hydroxy, and $R_4$ is a phenyl-alkanoyl group.

20. A compound according to claim 3 named N-(3,4-dimethoxyphenylacetyl)-5,6-dimethoxycyclopentano-1,2,3,4-tetrahydroisoquinoline.

21. A compound according to claim 3 named N-(3,4-dimethoxyphenylethyl)-5,6-dimethoxycyclopentano-1,2,3,4-tetrahydroisoquinoline.

22. A compound according to claim 3 named N-(diphenylacetyl)-5,6-dimethoxycyclopentano-1,2,3,4-tetrahydroisoquinoline.

23. A compound according to claim 2 in which R and $R_1$ are each the same alkoxy group, and $R_4$ is a alkanoyl group.

24. A compound according to claim 2 named N-methyl-5,6-diacetoxycyclopentano-1,2,3,4-tetrahydroisoquinoline.

* * * * *

UNITED STATES PATENT AND TRADEMARK OFFICE
CERTIFICATE OF CORRECTION

PATENT NO. : 3,962,254
DATED : June 8, 1976
INVENTOR(S) : Ian W. Mathison et al.

It is certified that error appears in the above-identified patent and that said Letters Patent are hereby corrected as shown below:

Abstract, <u>line 5 from end</u>, change "akanoyl" to --alkanoyl--; column 1, <u>line 36</u>, change "benzyhydryl" to --benzhydryl--; <u>line 58</u>, change "group" to --groups--; column 3, <u>line 1</u>, after "$R_5$" insert --and $R_6$--; <u>line 6</u>, change "dimehoxy" to --dimethoxy--; <u>line 8</u>, change "tetrhydro" to --tetrahydro--; <u>lines 34, 39 and 41</u>, change "pentao" to --pentano--; <u>line 41</u>, change "dimetoxy" to --dimethoxy--; column 6, <u>line 10</u>, after "[h]-" insert -- 1,2,3,4- --, change "dimethoxy" to --dihydroxy--; <u>line 12</u>, change "trimethoxy" to --trihydroxy--; <u>line 16</u>, change "pentao" to --pentano--; column 7, <u>line 7</u>, change "arakyl" to --aralkyl--; column 8, <u>line 27</u>, change "administered" to --administration--; column 10, <u>line 19</u>, change "relating" to --resulting--; column 11, <u>line 3 from bottom</u>, change "some" to --Some--; column 12, <u>last line</u>, change "off" to --of--; column 15, <u>line 17</u>, change "obtaned" to --obtained--; column 16, <u>line 16</u>, change "pecipitate" to --precipitate--; Claims 13 to 18, 20 to 22 and 24, <u>line 2</u>, after "pentano" insert --[h]--.

Signed and Sealed this

Thirty-first Day of August 1976

[SEAL]

Attest:

RUTH C. MASON
*Attesting Officer*

C. MARSHALL DANN
*Commissioner of Patents and Trademarks*